(12) United States Patent
Thompson et al.

(10) Patent No.: US 7,871,418 B2
(45) Date of Patent: Jan. 18, 2011

(54) APPLIER FOR FASTENER FOR SINGLE LUMEN ACCESS ANASTOMOSIS

(75) Inventors: Brian James Thompson, Cincinnati, OH (US); Mark S. Ortiz, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 609 days.

(21) Appl. No.: 11/847,363

(22) Filed: Aug. 30, 2007

(65) Prior Publication Data

US 2008/0221596 A1    Sep. 11, 2008

(30) Foreign Application Priority Data

Oct. 6, 2006    (EP) .................................. 06021066

(51) Int. Cl.
*A61B 17/08*    (2006.01)
(52) U.S. Cl. ...................................... 606/153
(58) Field of Classification Search ................ 606/151, 606/153
See application file for complete search history.

(56) References Cited

U.S. PATENT DOCUMENTS

| 2002/0091397 A1 | 7/2002 | Chen |
| 2005/0070926 A1* | 3/2005 | Ortiz .......................... 606/142 |

FOREIGN PATENT DOCUMENTS

EP    0 941 034 B1    5/2004

* cited by examiner

*Primary Examiner*—Gary Jackson
*Assistant Examiner*—Gregory Anderson

(57) ABSTRACT

An applier for an anastomosis ring device. The applier has an elongate implement portion and a handle connected to the implement portion. The applier further includes a distal actuating member having catch means which, in a lock position, protrudes radially outward to engage a distal ring. The applier further includes a proximal actuating member adapted to engage a proximal ring, and an actuation mechanism to approximate the proximal and distal rings. The distal actuating member is rotatable about a longitudinal axis from its lock position to a release position thereby sliding along a deviating surface at the implement portion.

18 Claims, 14 Drawing Sheets

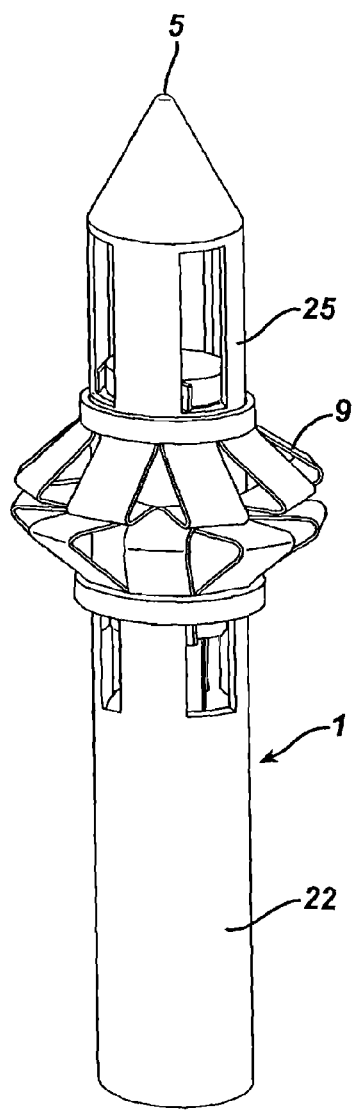
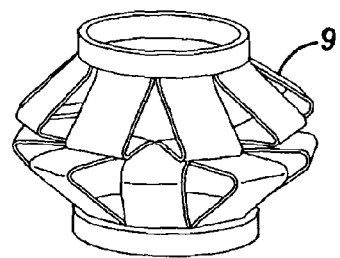
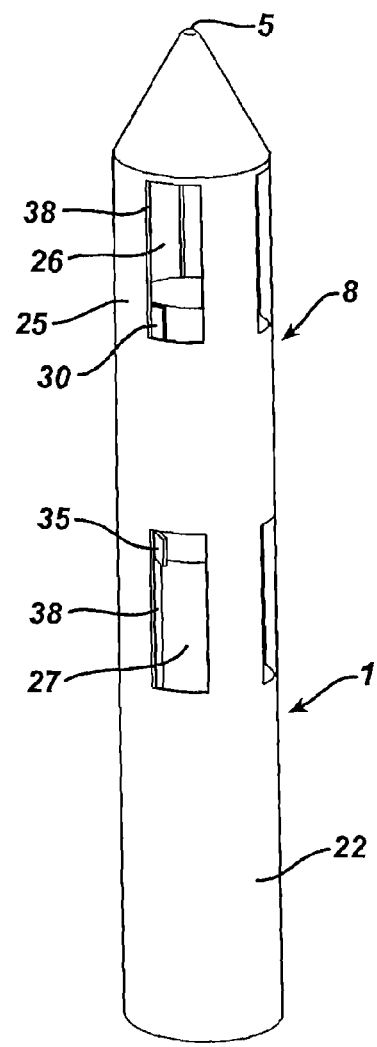
FIG. 5
FIG. 6

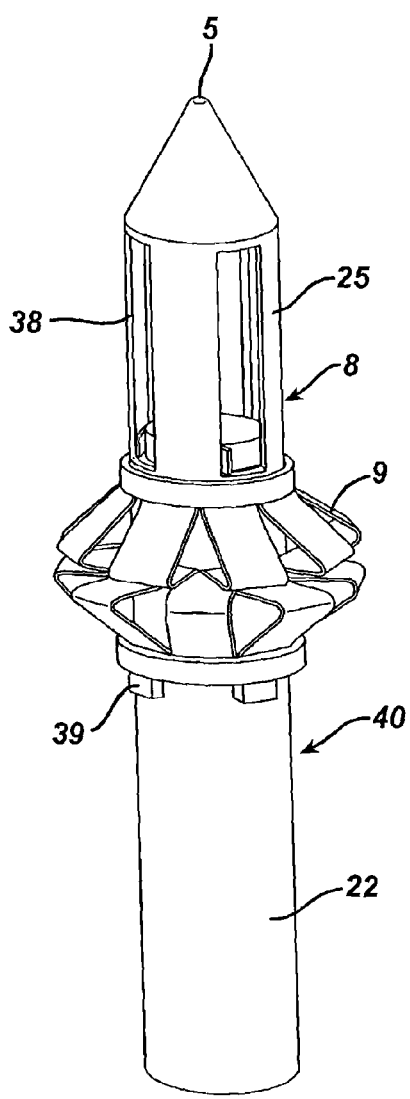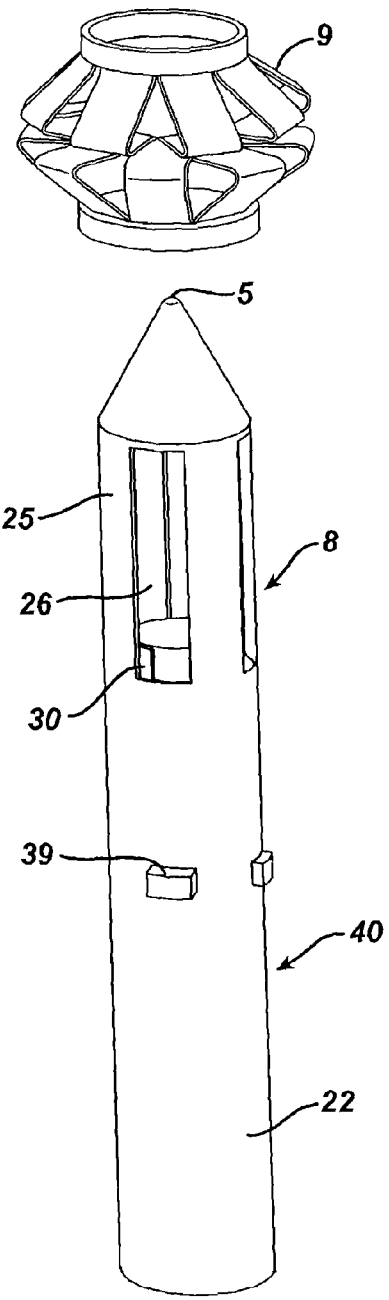
*FIG. 12*  *FIG. 13*

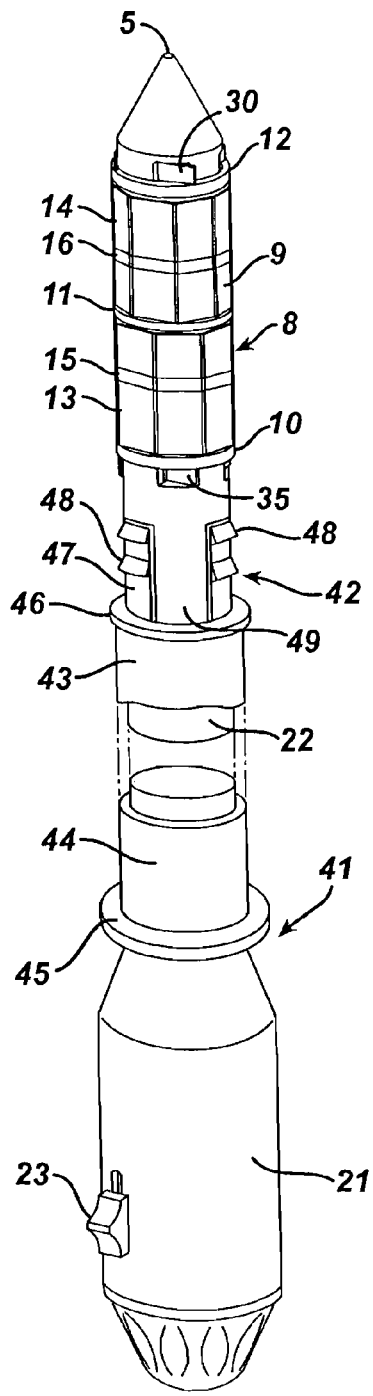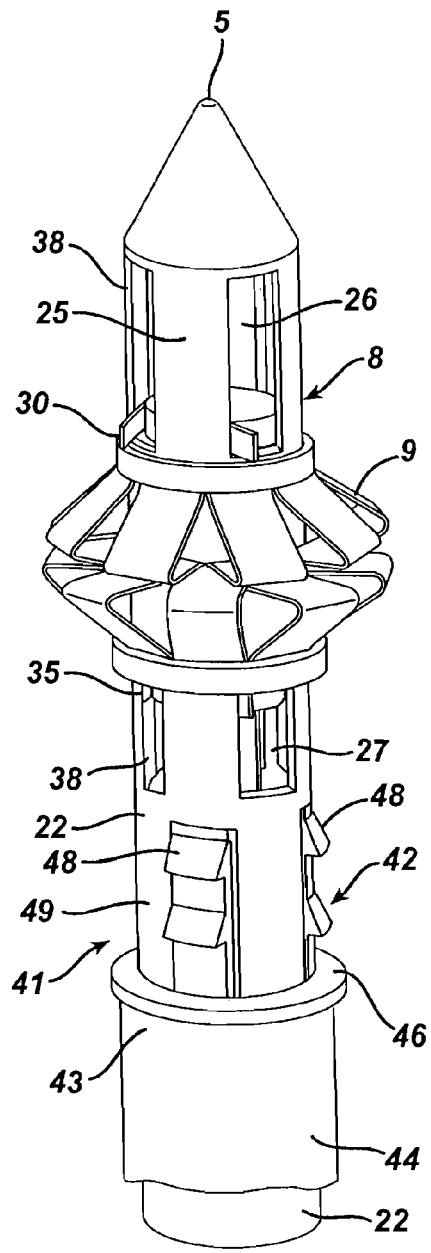
FIG. 14
FIG. 15

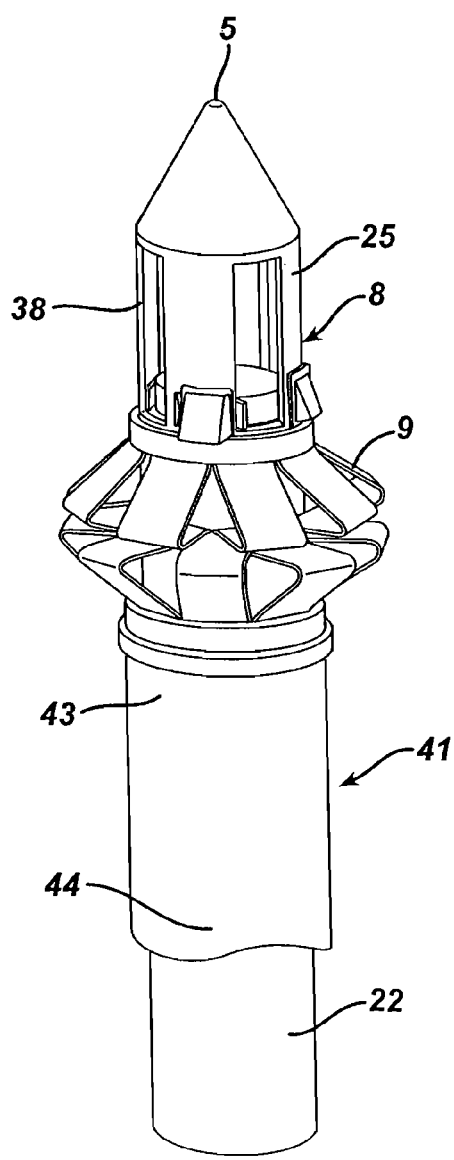
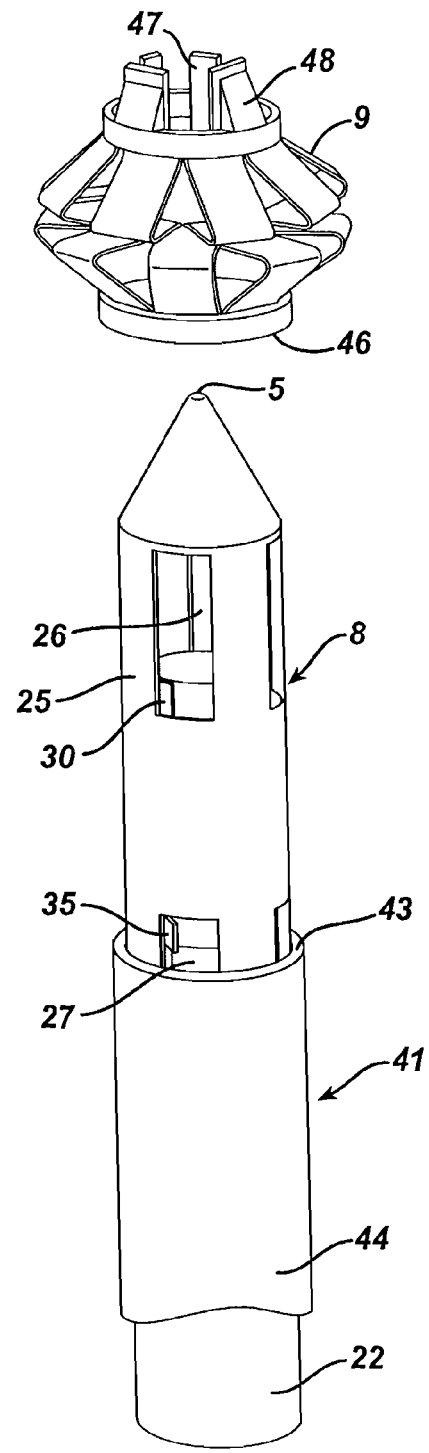
FIG. 16
FIG. 17

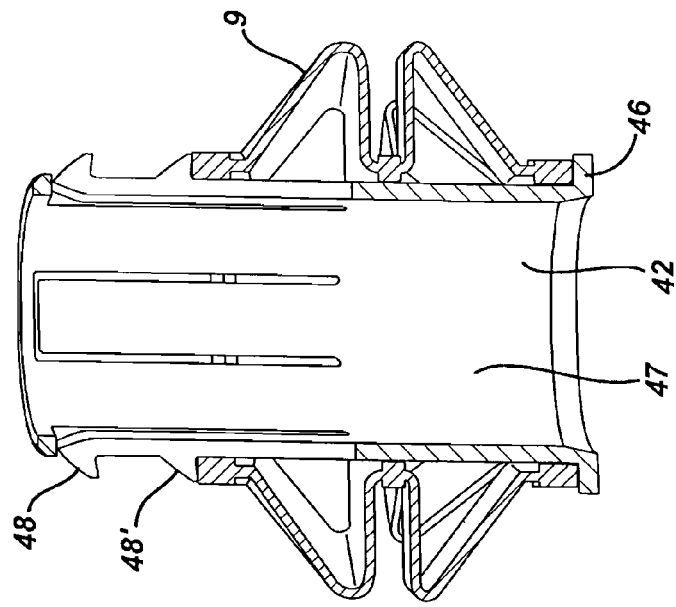
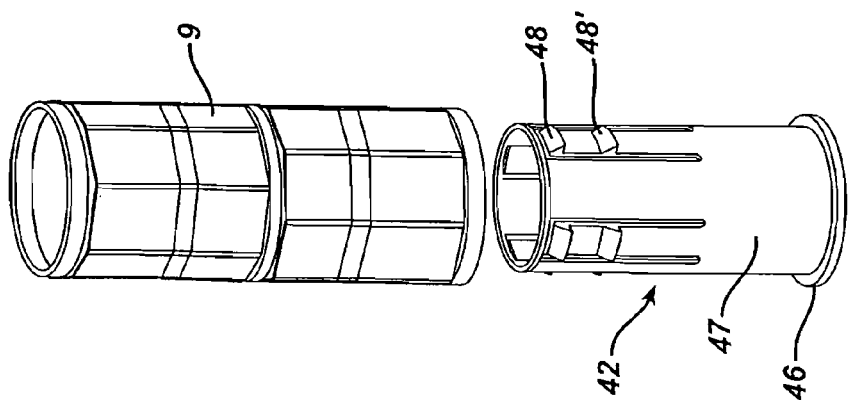

APPLIER FOR FASTENER FOR SINGLE LUMEN ACCESS ANASTOMOSIS

The present invention relates, in general, to devices and methods for surgically modifying organs and vessels. More particularly, it relates to anastomosis devices for joining two organs such as, for example, two separate lengths of small bowel to each other, a section of small bowel to the stomach, or the common bile duct to the duodenum in a procedure called a choledochoduodenostomy. Vascular anastomosis may be performed as well.

The percentage of the world population suffering from morbid obesity is steadily increasing. Severely obese persons are susceptible to increased risk of heart disease, stroke, diabetes, pulmonary disease, and accidents. Because of the effect of morbid obesity to the life of the patient, methods of treating morbid obesity are being researched.

Numerous non-operative therapies for morbid obesity have been tried with virtually no permanent success. Dietary counseling, behavior modification, wiring a patient's jaws shut, and pharmacological methods have all been tried, and though temporarily effective, failed to correct the condition. Further, introducing an object in the stomach, such as an esophago-gastric balloon, to fill the stomach have also been used to treat the condition; however, such approaches tend to cause irritation to the stomach and are not effective long-term.

Surgical treatments of morbid obesity have been increasingly used with greater success. These approaches may be generalized as those that reduce the effective size of the stomach, limiting the amount of food intake, and those that create malabsorption of the food that is eaten. For instance, some patients benefit from adjustable gastric bands (AGB) that are laparoscopically placed about the stomach to form a stoma of a desired size that allows food to fill an upper portion of the stomach, causing a feeling of satiety. To allow adjustment of the size of the stoma after implantation, a fluid conduit communicates between an inwardly presented fluid bladder of the AGB to a fluid injection port subcutaneously placed in front of the patient's sternum. A syringe needle may then inject or withdraw fluid as desired to adjust the AGB.

Although an effective approach to obesity for some, other patients may find the lifestyle changes undesirable, necessitated by the restricted amount of food intake. In addition, the medical condition of the patient may suggest the need for a more permanent solution. To that end, surgical approaches have been used to alter the portions of the stomach and/or small intestine available for digesting food. Creating an anastomosis, or the surgical formation of a passage between two normally distinct vessels, is a critical step of many surgical procedures. This is particularly true of gastric bypass procedures in which two portions of small intestine are joined together and another portion of small intestine is joined to the stomach of the patient. This is also true of surgery to alleviate blockage in the common bile duct by draining bile from the duct to the small intestine during surgery for pancreatic cancer.

With particular reference to gastric bypass procedures, current methods of performing a laparoscopic anastomosis for a gastric bypass include stapling, suturing, and placing biofragmentable rings, each having significant challenges. For instance, suturing is time consuming, as well as being technique and dexterity dependent. Stapling requires placement of an anvil, which is a large device that cannot be introduced through a trocar port. Having to introduce the port through a laparotomy presents an increased incidence of wound site infection associated with intralumenal content being dragged to the laparotomy entry site.

As an example of the latter approach, in U.S. Pat. No. 6,543,456 a method for gastric bypass surgery includes the insertion of proximal and distal anastomosis members (e.g., anvils) transorally with grasping forceps. The stomach and the small intestine are transected endoscopically by a surgical severing and stapling instrument to create a gastric pouch, a drainage loop, and a Roux limb. An endoscopically inserted circular stapler attaches to the distal anastomosis member to join the drainage loop to a distal portion of the intestine, and the circular stapler attaches to the proximal anastomosis member to join the Roux limb to the gastric pouch. Thereafter, the anastomosis members are removed to create an orifice between joined portions of the stomach and intestine. This method reduces the number of laparoscopic ports, avoids a laparoscopic insertion of an anastomosis instrument (e.g., circular stapler) into an enlarged surgical port, and eliminates the need for an enterotomy and an enterotomy closure. For many anastomoses, surgeons use circular staplers, linear staplers, or manual sutures. However, to reduce incision size and to make the surgical process less technically demanding and time consuming, single piece anastomotic devices have been proposed which are deformable during deployment by an anastomotic applier to hold tissue portions together. US 2005/0070926 A1 and US 2005/0070935 which are hereby incorporated herein by reference, describe an anastomotic applier having an implement portion that receives an anastomotic ring device with an unactuated shape of a cylinder with a proximal ring at one end and a distal ring at the other. The ring device further has proximal arms that are attached to the proximal ring and distal arms that are attached to the distal ring. Inwardly directed ends of the distal arms are coupled to inwardly directed ends of the proximal arms at a center ring such that the arms will outwardly actuate when the rings are drawn closer together during actuation of the applier. A latching mechanism locks the rings in this actuated shape of a rivet. The applier comprises radially protruding catches which engage the ring such that the spacing of the distal ring to the center ring and the spacing of the proximal ring to the center ring may be reduced by a translational movement of the catches. In order to remove the applier from the actuated and latched ring device, proximal to each catch is a release ramp that causes the catch to move inwardly as the release ramp contacts the next more proximal ring at full actuation. The anastomotic applier and ring device disclosed in US 2005/0070926 A1 and US 2005/0070935 make it possible to perform a single lumen access anastomosis through existing trocar ports and to create an anastomotic attachment between lumens obviating the need for surgical stapling and suturing.

Nonetheless, this known devices have the disadvantage that the release mechanism is triggered firstly in response to an axial movement of the catches which results in a deformation of the ring device and, secondly, in response to direct contact of the release ramps with the ring device. As a consequence, the applier can deploy the ring device with only one preset ring deformation, otherwise withdrawal of the applier from the deployed ring device would be impossible. This means that different appliers must be provided for different tissue thicknesses or different tissue compressions and an adjustment of the tissue compression during deployment (i.e. adjustment of the distance between the distal and proximal rings) of the ring device is impossible.

The object of the present invention is therefore to improve the known anastomotic applier such that an adjustment of the ring compression or ring approximation (i.e. tissue thickness) and the use of adjustable ring devices becomes possible.

These and other objects are achieved by an anastomotic applier according to the annexed claim 1. Advantageous embodiments are the object of the dependent claims.

According to the invention, an applier is proposed for an anastomosis ring device of the type having proximal, center, and distal rings connected respectively by proximal and distal hinged arms, the hinged arms having a generally oblong radially retracted shape when the ring device is unactuated and a folded radially protruding shape when the ring device is actuated. The applier comprises an elongate implement portion, a handle connected to the implement portion, a distal actuating member comprising catch means which, in a lock position, protrudes radially outward to engage the distal ring, a proximal actuating member adapted to engage the proximal ring, an actuation mechanism arranged at the handle and configured to cause the proximal and distal actuating members to move towards each other along a longitudinal axis of the implement portion to approximate the proximal and distal rings causing actuation of the hinged arms, wherein the distal actuating member is rotatable about said longitudinal axis from said lock position to a release position thereby sliding along a deviating surface at the implement portion, which is configured to urge said catch means radially inward to disengage it from the distal ring. Thanks to the rotational release movement about the longitudinal axis of the implement portion, the release is independent from the axial translation of the actuating member and, hence, from the state of deformation of the ring device. This makes it possible to use the anastomotic applier for deploying adjustably latchable ring devices realizing different ring distances and different tissue pressures. Moreover, by providing a deviating surface at the implement portion of the applier instead of forming it on the ring device, the design of the ring device can be optimized for the anastomotic attachment of the two tissue portions without taking account of the applier structure. Similarly, the applier is more versatile and less dependent from the ring device. As a result, different ring devices (all having of course substantially the previously described general features) can be deployed by the anastomotic applier.

In accordance with an advantageous embodiment of the invention, the actuation mechanism is adapted to move the proximal actuating member distally and to move the distal actuating member proximally causing actuation of the hinged arms of the ring device, while leaving the central ring substantially stationary on the implement portion. By contemporaneously moving both actuating members towards each other it becomes possible to deploy and deflect the anastomotic ring device from its original cylindrical shape to the actuated rivet shape avoiding movements of the applier with respect to the tissue. With the prior art techniques, such an applier movement was necessary to compensate the movement of the centre of the ring device along the implement shaft. According to a yet further aspect of the invention, the actuating mechanism is adapted to axially translate the proximal actuating member independently from the axial translation of the distal actuating member and vice versa. This enables the applier to selectively actuate only one group of the distal and proximal hinged arms, respectively, in order to assist or improve tissue positioning and approximation prior to tissue clamping. Moreover, the independent translational movement of the proximal and distal actuating members makes it possible to translate the ring device (i.e. the centre ring thereof) in a controlled manner along the implement portion, e.g. during or prior to deployment and actuation of the hinged arms.

In accordance with an alternative embodiment of the invention, the actuating mechanism is adapted to axially translate the distal actuating member, while the proximal actuating member comprises a distally facing stationary arresting surface formed at the implement portion, resulting in a particularly simple and sturdy actuating mechanism and applier in general. As will be immediately appreciated by the skilled person, by pulling the distal actuating member proximally towards the arresting surface, the ring device will be contemporaneously translated proximally and deformed in its actuated rivet shape.

Turning again to the release mechanism of the applier, according to an aspect of the invention, the implement portion comprises a substantially cylindrical housing with axially extending distal window slots and the distal actuating member comprises a shaft slidably received inside the housing and a plurality of fin shaped catches which protrude outward from the shaft and extend through the window slots such that they engage the distal ring of the anastomotic ring device, when in the lock position. In this lock position, the fins can extend radially to tangentially or inclined at an angle between the radial and tangential orientation. Preferably, the fins are inclined or slanted in a direction opposite the direction of rotation of the actuating member from the lock position to the release position, thereby facilitating the inward deviation of the fins by the lateral longitudinal edges of the corresponding distal window slots which act as the above mentioned deviating surfaces.

According to a preferred embodiment, the cylindrical housing further defines a plurality of axially extending proximal window slots and the proximal actuating member comprises a shaft slidably received inside the housing and a plurality of fin shaped catches which protrude outward from the shaft and extend through the proximal window slots such that they engage the proximal ring of the anastomotic ring device, when in the lock position. The arrangement, shape and release mechanism of the proximal catches is preferably identical to that of the previously described distal catches. The distal and proximal window slots can also be longitudinally connected and continuous so that the proximal and distal portion of the same window slot act as the proximal and distal window slots, respectively.

Advantageously, the proximal and distal actuating members are arranged axially slidably to one another but coupled in rotation about the longitudinal axis of the implement portion such that the distal and proximal catches can be simultaneously brought in the release position by a single common rotational movement of both actuating members with respect to the housing of the implement portion.

These and other features and advantages of the present invention shall be made apparent from the accompanying drawings which illustrate embodiments of the invention, and, together with the general description of the invention given above, and the detailed description of the embodiments given below, serve to explain the principles of the present invention.

FIG. 5 is a perspective detail view of the implement portion of the applier carrying the single lumen access deployable ring, the ring being in a folded actuated configuration and the applier actuating members being retracted in a release position;

FIG. 6 is a perspective detail view of the implement portion of the applier and the single lumen access deployable ring, the ring being in a folded actuated configuration and the applier being removed through the center of the ring.

FIG. 10 to 13 show different operational configurations of an applier according to a second embodiment of the invention.

FIG. 14 to 17 show different operational configurations of an applier according to a third embodiment of the invention.

FIG. 18 to 22 illustrate different embodiments of a detachable adjustable snapper element of the applier according to the invention.

Figure 1:
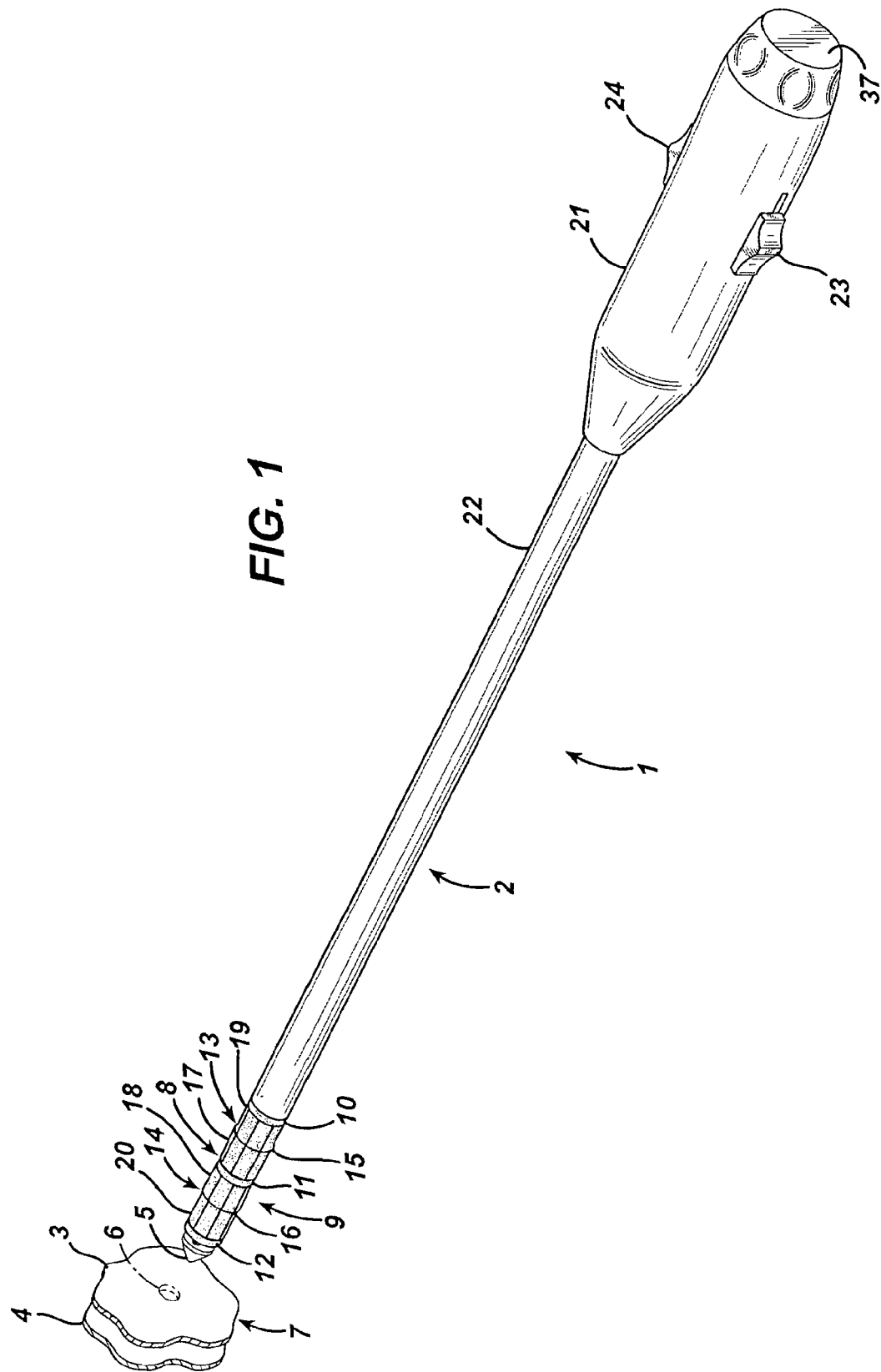
FIG. 1 is a perspective view of a single lumen access deployable ring for intralumenal anastomosis installed upon an applier being inserted laparoscopically to an anastomosis target site on each of two portions of a patient's small intestine.

Turning to the Drawings, wherein like numerals denote like components throughout the several views, FIG. 1 depicts an applier 1 having an elongate implement portion 2 dimensionally sized for insertion through a cannula of a trocar or laparoscopic port to tissue walls 3, 4 to anastomose two lumens. A distal introducer tip 5 of the applier 1 pierces through an opening 6 at an anastomosis site 7 to position an actuating portion 8 that holds a ring device 9 for single lumen anastomosis. The ring device 9 has three primary rings, depicted as a proximal ring 10, a center ring 11, and a distal ring 12, that are cylindrically aligned with one another. The proximal ring 10 is longitudinally attached to the center ring 11 by proximal arms 13, which in turn is longitudinally attached to the distal ring 12 by distal arms 14. Each proximal and distal arm 13, 14 is bisected respectively by a hinged joint 15, 16 defining an inner arm segment 17, 18 also hingedly attaching to the center ring 11 and an outer arm segment 19, 20 also hingedly attached to the respective proximal or distal ring 10, 12. In its unactuated state as depicted in FIG. 1, the arms 13, 14 are substantially oblong and the ring device 9 is at least approximately cylindrical. The relative lengths of the inner arm segments 17, 18 to outer arm segments 19, 20 may be selected to provide a desired angular contact to tissue walls 3, 4. In the illustrative version, the relationship resembles a cantilevered contact with the inner arm segments 17, 18 actuating to an approximately parallel relationship to the tissue walls 3, 4.

A handle portion 21 is proximally connected to a shaft 22 of the implement portion 2. The shaft 22 may be rigid or flexible, with the latter being desirable for intralumenal insertion, such as through the esophagus. The handle 21 includes controls for longitudinally positioning the rings 10, 11, 12 of the ring device 9. In the illustrative version, this includes a distal ring slide control 23 and a proximal ring slide control 24. Although a manually positioned and actuated applier 1 is depicted for clarity, it should be appreciated that a remotely positioned and actuated applier may be used consistent with aspects of the invention, for instance to allow placement in a more controlled manner, to avoid disturbing an imaging modality, or for other reasons. The handle 21 may further include controls for a distal tip illumination capability so that actuation of the distal arms 14 in the distal lumen may be proximally viewed from an endoscope. It will be appreciated that the terms "proximal" and "distal" are used herein with reference to a clinician gripping the handle portion 21 of the applier 1.

Figure 2:
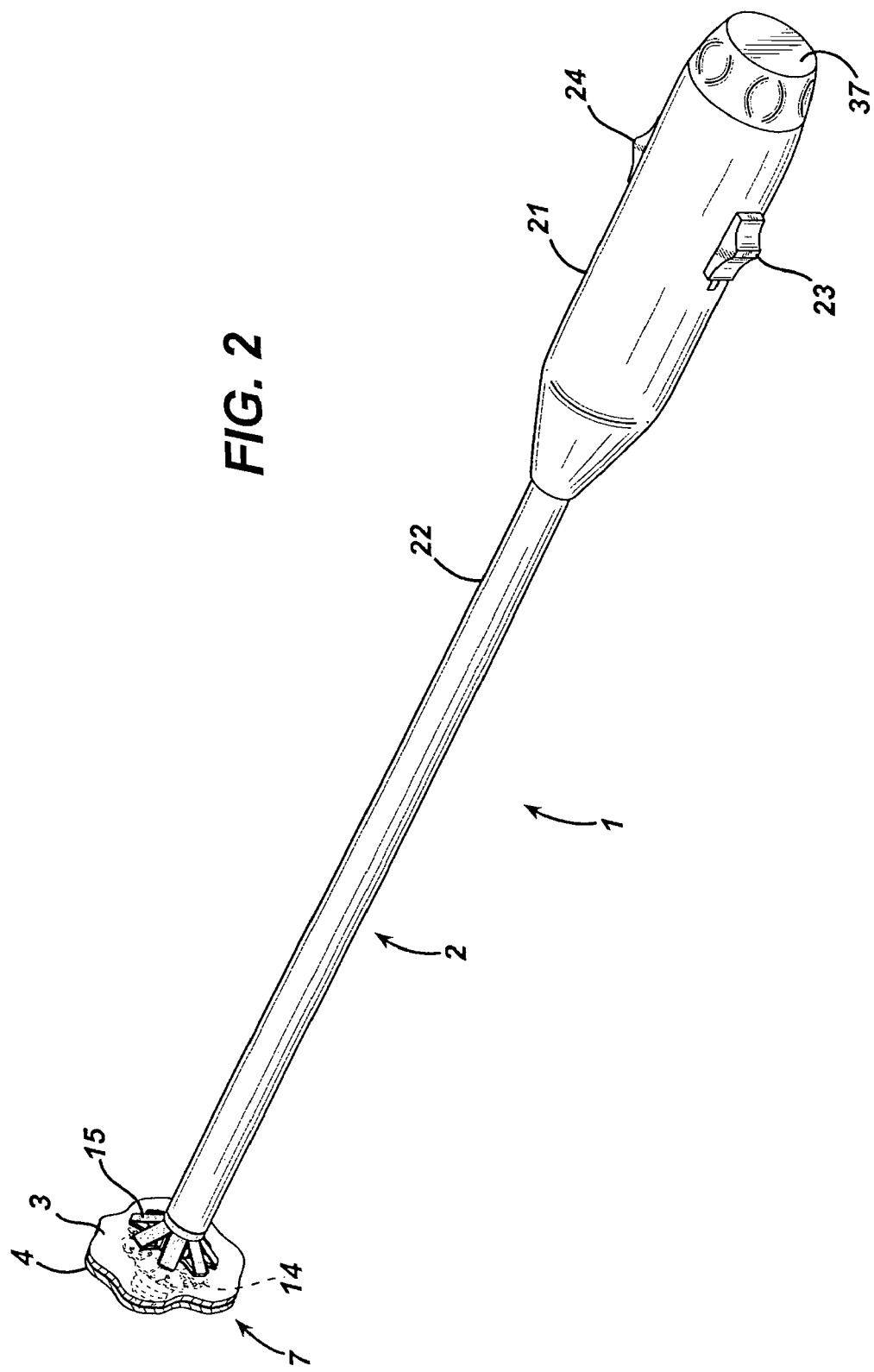
FIG. 2 is the applier of FIG. 1 after actuation of the single lumen access deployable ring to appose the two portions of small intestine.

In FIG. 2, the distal ring slide control 23 has been withdrawn proximally and the proximal ring slide control 24 has been advanced distally so that both the distal ring 12 and proximal rings 10 are brought into locking proximity of the center ring 11, which remains substantially stationary. In response thereto, the proximal and distal arms 13, 14 hinge outwardly from the longitudinal axis of the ring device 9, creating a hollow rivet or hourglass shape for apposing tissue walls 3, 4. The center ring 11 sits at a tissue junction between lumens and the distal and proximal rings 12, 10 come to rest in respective lumens. By latching rings 10, 11, 12 one to another when actuated, the ring device 9 is held in the actuated position with bent arms 13, 14 apposing tissue. The proximal arms 13 may be staggered, as depicted, from distal arms 14 to create a tortuous path for the compressed tissue. Alternatively, the arms 13, 14 may be aligned to directly mate to each other. FIGS. 3 to 8 illustrate the applier 1 according to a first embodiment of the invention.

The implement portion 2 comprises a substantially cylindrical housing 25 which defines, in the zone of the actuating portion 8, a plurality of axially extending distal window slots 26 and a plurality of axially extending proximal window slots 27 which extend along the track of the actuation movement of the distal and proximal rings 12, 10, respectively.

A distal actuating member 28 comprises a shaft 29 slidably received inside the housing 25 and operatively connected with the distal ring slide control 23 via a pull rod 31. A plurality of fin shaped distal catches 3Q protrude outward from the shaft 29 and extend through the distal window slots 26 such that they engage a distal end surface of the distal ring 12, when in the lock position. In this condition, it is possible to move the distal ring 12 proximally by shifting the distal ring slide control 23 in proximal direction.

Similarly, a proximal actuating member 32 comprises a shaft 33 slidably received inside the housing 25 and operatively connected with the proximal ring slide control 24 via a push rod 34. A plurality of fin shaped proximal catches 35 protrude outward from the shaft 33 and extend through the proximal window slots 27 such that they engage a proximal end surface of the proximal ring 10, when in the lock position. In this condition, it is possible to move the proximal ring 10 distally by shifting the proximal ring slide control 24 in distal direction.

Figure 9:
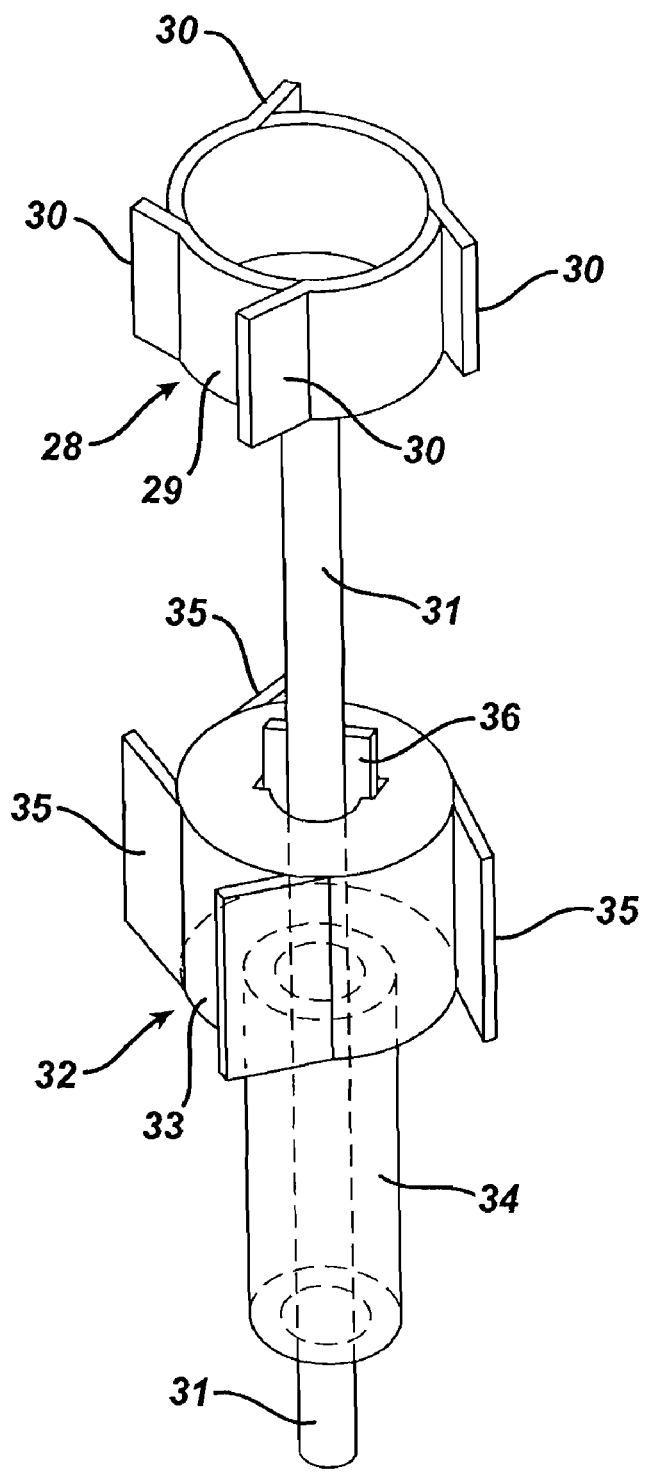
FIG. 9 is a schematic perspective view of a detail of the actuating mechanism of the applier according to an illustrative embodiment of the invention.
Figure 9A:
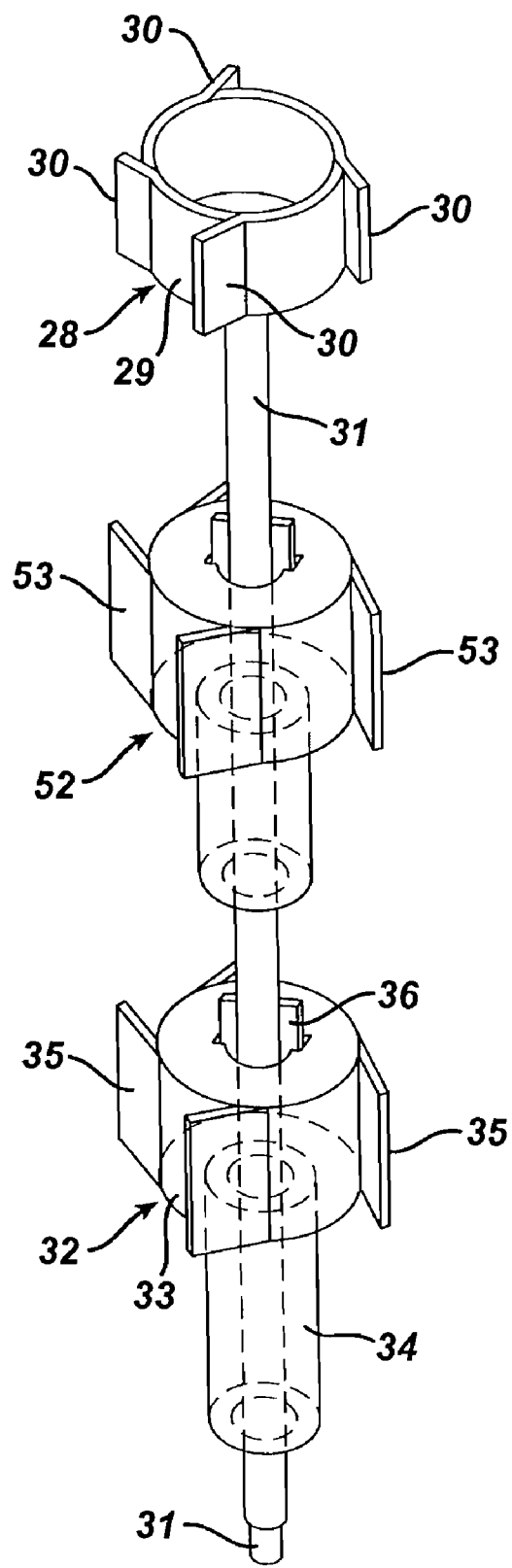
FIG. 9A is a schematic perspective view of a detail of the actuating mechanism of the applier according to a second illustrative embodiment of the invention.
Figure 10:
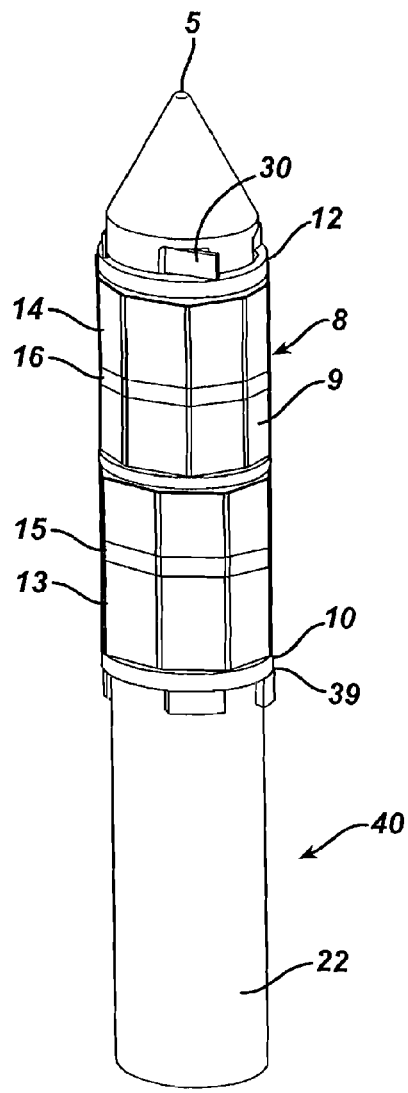
Figure 11:
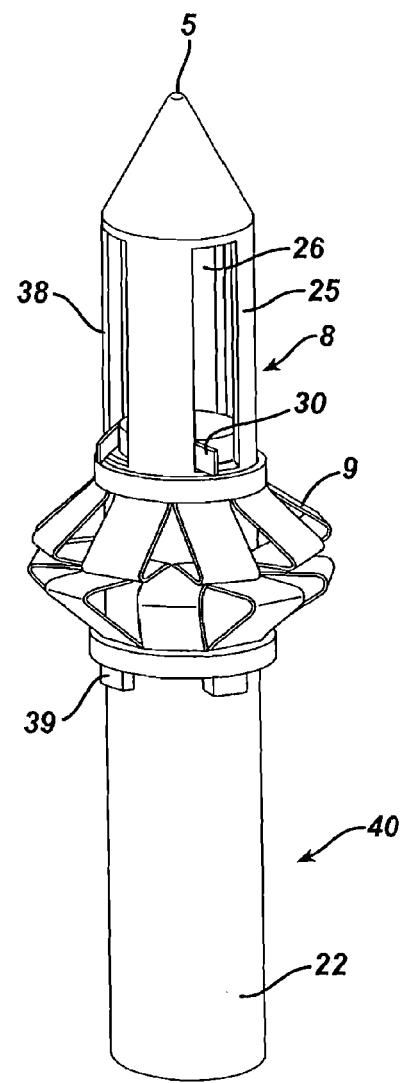
Figure 21:
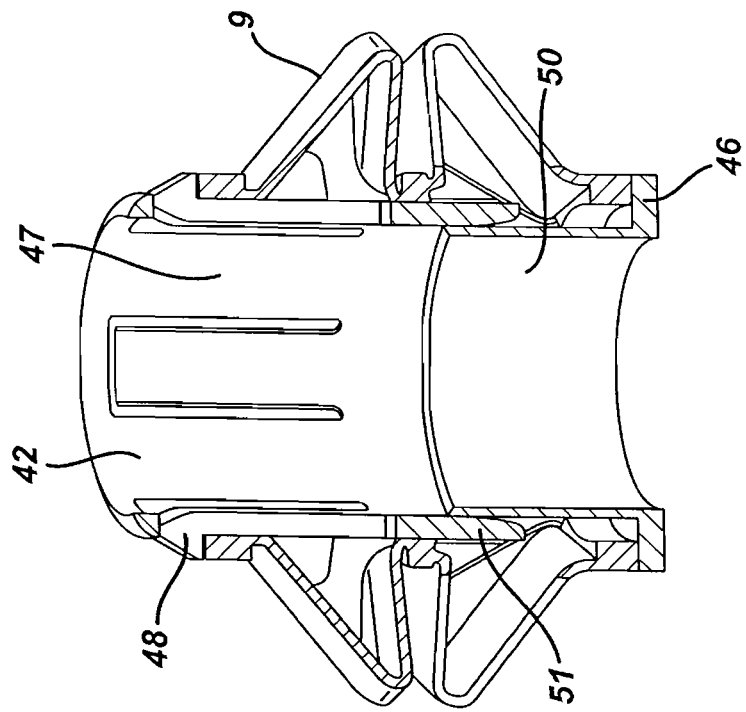

As schematically illustrated in FIG. 9, the proximal and distal actuating members 28, 32 are configured to translate relative to each other (and preferably independently from one another), but they are advantageously locked to each other in rotation about the longitudinal axis X of the implement portion 2, e.g. by a geometric coupling 36.

The handle 21 comprises a release control, e.g. a rotating knob 37, coupled to the pull rod 31 and/or to the push rod 34 and adapted to rotate at least the distal actuating member 28 (and preferably both actuating members 28, 32) about the longitudinal axis X of the implement portion 2 from the lock position to a release position in which the catches 30, 35 are disengaged from the anastomotic ring device 9 such that the implement portion of the applier can be proximally withdrawn through the center opening of the ring device 9.

As already mentioned above, according to the invention, the disengaging of the applier 1 from the ring device 9 is obtained by the feature that, during the rotation of the actuating member 28, 32, a part of the latter slides along a deviating surface at the implement portion, particularly at the housing 25, which is configured to urge the catches 30, 35 radially inward to disengage them at least from the distal ring 12. The skilled person will appreciate that, in order to withdraw the applier from the ring device, the proximal catches need not necessarily be retracted.

In accordance with the embodiments illustrated in the figures, the catches 30, 35 are preferably inclined or slanted in a direction opposite the direction of rotation from the lock position to the release position, thereby facilitating the inward deviation of the catches by lateral longitudinal edges 38 of the corresponding window slots 26, 27 which embody the above mentioned deviating surfaces.

In the illustrative version, the housing 25 and each actuating member 28, 32 is formed from a rigid polymer or sheet metal.

Figure 3:
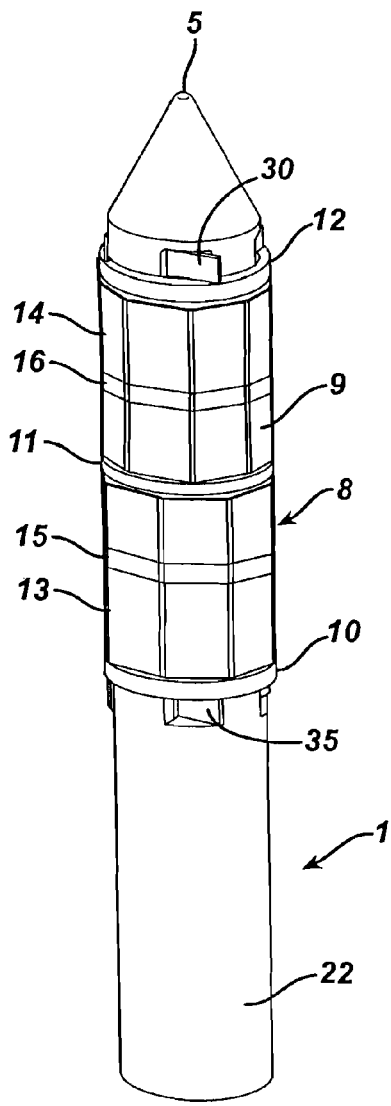
FIG. 3 is a perspective detail view of the implement portion of the applier carrying the single lumen access deployable ring, the ring being in an oblong un-actuated configuration and the applier actuating members being in a lock position.

In FIG. 3, the oblong un-actuated ring device 9 is applied to the actuating portion 8 of the applier 1 and the distal 30 and proximal catches 35 protrude outward through the corresponding window slots 26, 27 and engage the distal and proximal rings 12, 10 of the ring device 9.

Figure 4:
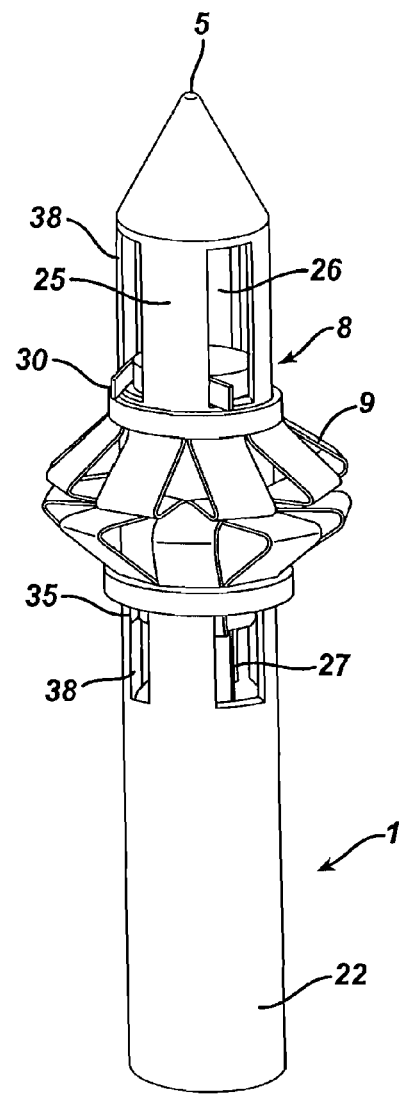
FIG. 4 is a perspective detail view of the implement portion of the applier carrying the single lumen access deployable ring, the ring being in a folded actuated configuration and the applier actuating members being still in the lock position.
Figure 7:
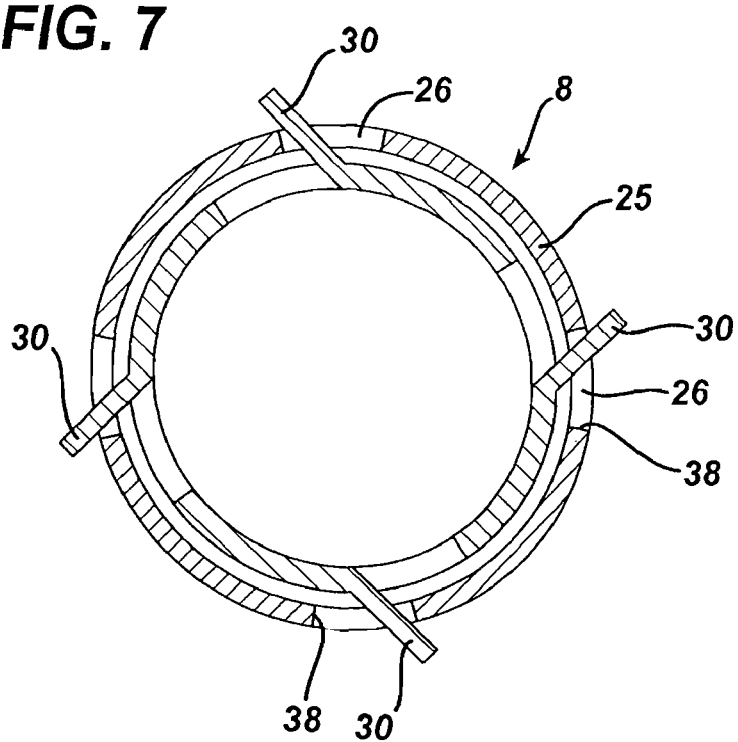
FIGS. 7 and 8 are enlarged sectional views of the actuating portion of the applier in the lock position and release position, respectively.
Figure 8:
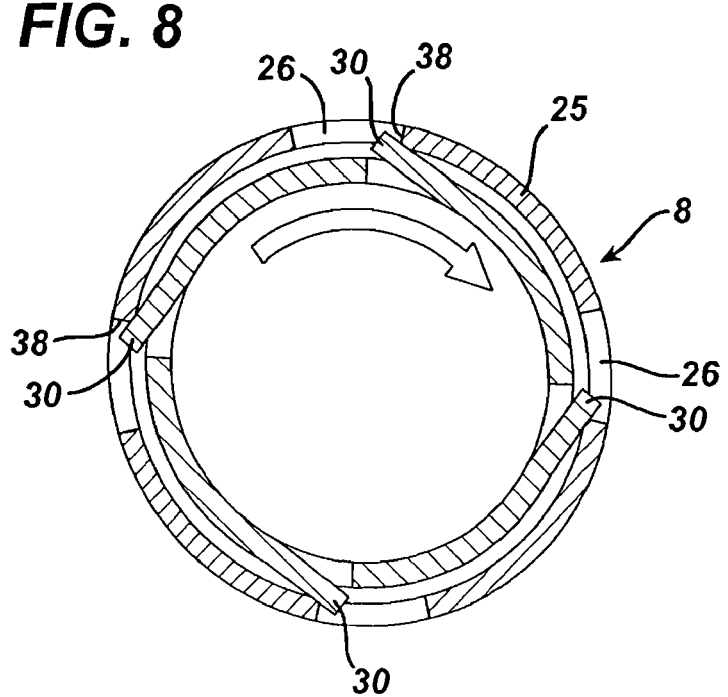

FIG. 4 illustrates the situation after the distal ring slide control 23 has been shifted proximally and the proximal ring slide control 24 has been shifted distally, causing the actuating members 28, 32 to approximate the distal ring 12 and the proximal ring 10 toward the center ring 11 and the ring device 9 to latch in its actuated rivet shape thanks to a not shown latch feature. In this configuration the distal and proximal catches 30, 35 are still in their lock position, i.e. they protrude outward and inhibit withdrawal of the applier 1 from the actuated ring device 9.

FIG. 5 illustrates the situation after the release control 37 has been rotated, thereby rotating the actuating members 28, 32 about the longitudinal axis X from the lock position into the release position, in which the catches 30, 35 are bent inwardly by the window edges 38 and disengage from the ring device 9. It is now possible to remove the applier 1 proximally through the center opening of the actuated and deployed ring device 9, as shown in FIG. 6.

FIG. 9 to 12 illustrate an anastomotic applier 40 according to a second embodiment of the invention, in which the proximal actuating member and the proximal ring slide control are obviated and replaced by stationary proximal arresting surfaces 39 adapted to contact the proximal end surface of the proximal ring 10, while the distal actuating member 28 is substantially embodied as described with reference to the embodiment of FIGS. 3 to 7, with the exception that the moving track of the distal catches 30 and hence the length of the distal window slots 26 and the length of the sliding track of the distal ring slide control 23 correspond to the entire actuation length of the ring device 9.

In accordance with a third embodiment, illustrated in FIGS. 14 to 17, the applier 41 comprises a latching mechanism adapted to carry a detachable snapper part 42 separate from the ring device 9 and suitable to snap connect the proximal ring 10 with the distal ring 12 in order to latch the ring device 9 in its actuated rivet shape. The latching mechanism comprises one or more longitudinally translatable push portions 43 arranged proximally with respect to the proximal catches 35 or the proximal arresting surface 39 and adapted to engage a proximal end surface of the snapper part 42 and to push the snapper part 42 distally in engagement with the anastomotic ring device 9. The push portions 43 are connected, via a push rod (for instance a tubular push rod 44 externally applied to the implement portion 2) to a dedicated latching slide control, for instance a flange portion 45 of the push rod 44 arranged near the handle portion 21. This allows to latch the ring device 9 after its actuation, thereby obviating to automatic latching which might disturb fine adjustment of the ring approximation and of the pressure applied to the tissue walls 3, 4 clamped by the ring device 9.

In accordance with the embodiment, the snapper part 42 comprises an annular proximal shoulder 46 suitable to engage the proximal end surface of the proximal ring 10 and a longitudinal portion 47 which protrudes distally from the proximal shoulder 46 and forms elastically supported snapper teeth 48 extending radially outwardly from the longitudinal portion 47 to enable snap engagement of the distal ring 12. The longitudinal portion 47 and the snapper teeth 48 of the snapper part define slots 49 or window openings in alignment with the proximal catches 35 or arresting surfaces 39 and, preferably, also in alignment with the distal catches 30 of the applier 1; 40; 41 to enable the snapper part 42 to be pushed in engagement with the distal ring 12 without interfering with the actuating members 28, 32 of the applier 1.

According to an embodiment, the snapper part 42 is adapted to latch the ring device 9 at different adjustable distances between the proximal ring 10 and the distal ring 12. This feature, together with the above described ring release mechanism of the applier which is suitable to release the ring device independently from the particular actuated configuration of the ring device, make it possible to deploy the anastomotic ring device at different tissue thicknesses and pressure rates and to adjust the ring configuration and tissue pressure during the application of the ring device.

In accordance with a first illustrative embodiment (FIG. 18, 19) of the snapper part 42, a plurality of snapper teeth 48, 48' (at least two of them) is arranged in a row which extends in the longitudinal direction of the longitudinal portion 47 such that the distances between the annular proximal shoulder 46 and the different snapper teeth 48, 48' of a same row correspond to different adjustable distances between the proximal and distal rings 10, 12 of the ring device 9.

Figure 20:
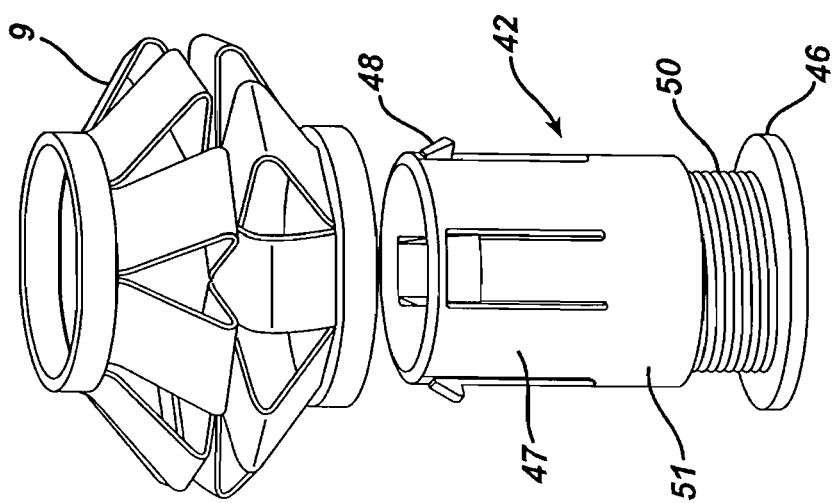

In accordance with a second illustrative embodiment (FIG. 20, 21), the longitudinal portion 47 of the snapper part 42 defines only one circumferential row of snapper teeth 48 (at least two diametrically oppositely arranged snapper teeth) suitable to snap engage the distal ring 12, but the annular proximal shoulder 46 comprises a distally projecting externally threaded adjusting portion 50 which mates an internal thread provided at the proximal base 51 of the longitudinal portion 47 such that the distance between the shoulder 46 and the snapper teeth 48 is adjustable by screwing the adjusting portion 50 more or less into the longitudinal portion 47. In order to adapt the snapper part to the actuating mechanism of the applier, also the threaded adjusting portion 50 might be slotted in order not to interfere with the catches 35 or arresting surfaces 39 during latching. In this particular embodiment, the screw adjustment must be performed in angular steps which correspond to the angular offset of the slots 49 or catches 30, 35, respectively.

Turning back to the embodiment of FIGS. 14 to 17, the flange portion 45 of the tubular push rod 44 apart from embodying a latching slide control (translational latching movement), preferably embodies also a rotational adjusting control for rotating the push portion 43 about the longitudinal axis of the implement portion 2. To this end, the push portion 43 comprises preferably geometrical coupling means (e.g. teeth, recesses) suitable to engaging the annular shoulder 46 of the snapper part 42 so that a rotational adjusting movement of the push portion 43 causes the annular shoulder 46 to screw into or unscrew from the longitudinal portion 47.

Figure 22:
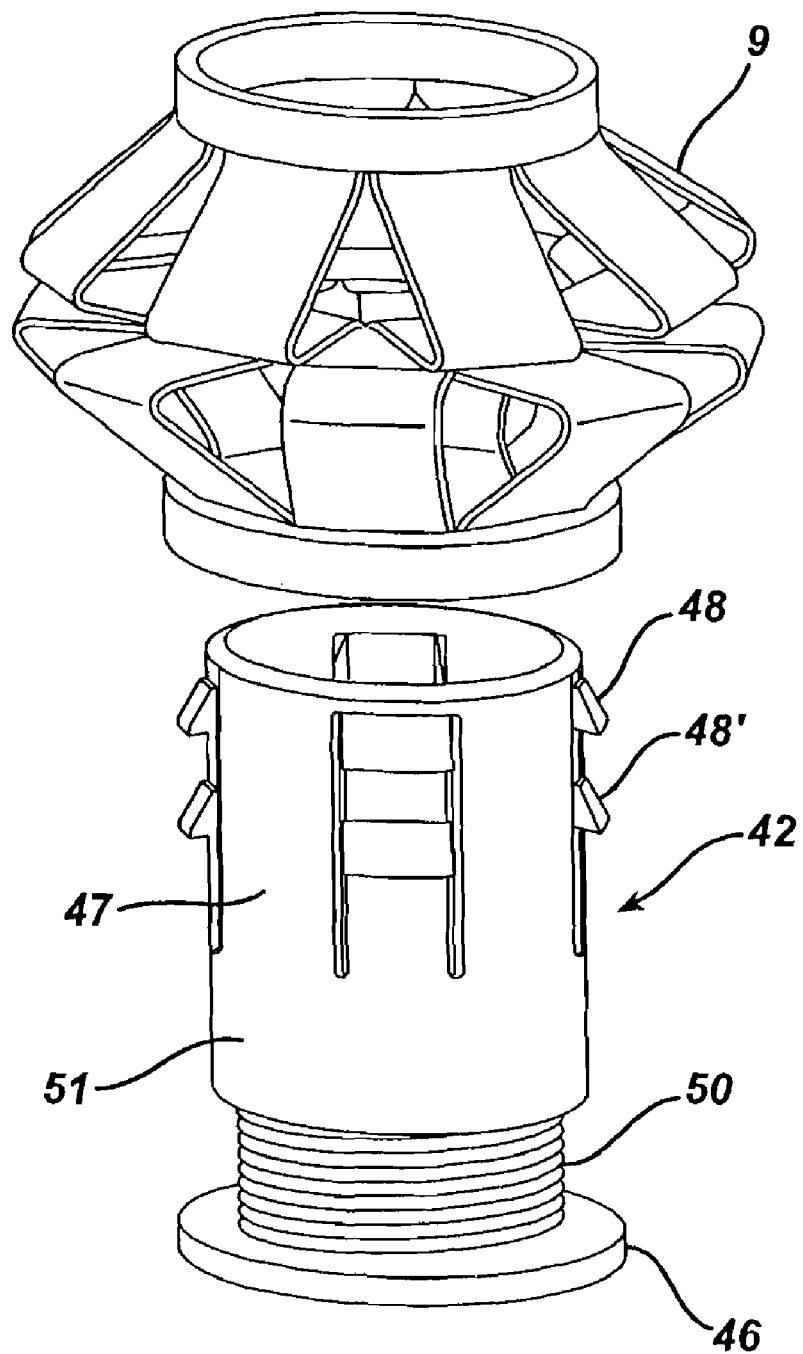

In accordance with a third illustrative embodiment (FIG. 22), the snapper part 42 comprises coarse adjustment means and additional fine adjustment means. The coarse adjustment means are embodied by a plurality of snapper teeth 48, 48' (at least two of them) arranged in a row which extends in the longitudinal direction of the longitudinal portion 47 such that the distances between the annular proximal shoulder 46 and the different snapper teeth 48, 48' of a same row correspond to different coarsely adjustable distances between the proximal and distal rings 10, 12 of the ring device 9. The fine adjustment means are embodied by an externally threaded adjusting portion 50 which protrudes distally from the annular proximal shoulder 46 and mates an internal thread provided at the proximal base 51 of the longitudinal portion 47. In this way, the distance between the shoulder 46 and the selected snapper tooth 48 is fine adjustable by screwing the adjusting portion 50 more or less into the longitudinal portion 47.

According to a yet further embodiment (not illustrated in the figures) the snapper part 42 itself defines a seat for receiving a group of needles or staples such that, in response to a distal movement of the push portion 43, the snapper part 42 moves in snap engagement with the rings 10, 12 and pushes contemporaneously the group of needles or staples in the anastomotic ring device 9 thereby piercing the tissue 3, 4 held between the proximal and distal ring arms. In this case, the group of needles might advantageously comprise a self supporting needle ring which can be arranged on the annular shoulder 46 of the snapper part 42.

In accordance with a further embodiment of the invention, whose features are compatible and combinable with those described and illustrated in connection with the previous embodiments, the applier 1 further comprises a central actuating member 52 arranged between the proximal 32 and distal actuating member 28 and having catch means 53 adapted to engage the central ring 11 of the ring device to hold it stationary during the actuating movement of the distal and/or proximal actuating members.

In order to axially lock the position of the center ring 11, the catch means 53 of the central actuating member 52 comprises suitable locking surfaces which protrude radially outward and mesh with corresponding recesses or locking surfaces of the center ring 11 or which embrace the center ring or part of it such that an axial movement of the latter is prevented in both proximal and distal direction.

According to one embodiment, the central actuating member 52 is axially stationary but rotatable about the longitudinal axis X from a lock position to a release position thereby sliding along a deviating surface at the implement portion 2, which is configured to urge the catch means 53 radially inward to disengage it from the central ring 11, as has been described in connection with the distal or proximal actuating members.

According to a further embodiment, the central actuating member 52 itself can also be axially moved proximally towards the proximal actuating member and/or distally towards the distal actuating member by means of a central ring slide control (not in the figures) which is preferably configured as described in connection with the distal and proximal ring slide controls 23, 24.

In particular, the stationary position or longitudinal translation of the central actuating member 52 is preferably maintainable or performable independently from the actuating movements of the proximal and/or distal actuating members.

As the release operation of the actuating members from the ring device is concerned, according to an embodiment the central 52 and distal 28 actuating members or the central 52, distal 28 and proximal 32 actuating members are arranged in an axially slidable but rotationally coupled relationship, such that the distal central and proximal catches can be simultaneously brought in their release position by a single common rotational movement about the longitudinal axis X of all actuating members with respect to the housing 25.

In use, the ring device 9 is received upon the actuating portion 8 of the implement portion 2 of the applier 1. Specifically, the proximal ring 10 of the ring device 9 rests against the proximal catches 35 and the distal catches 30 of the distal ring actuating member 28 engage the distal ring 12 of the ring device 9. A clinician manipulates the handle 21 to insert the implement portion 2 through the cannula of a trocar, laparoscopic port, or through a lumen such as the esophagus to the anastomosis site 7. The tissue walls 3, 4 are distally placed (from the surgeon point of view) and the introducer tip 5 of the implement portion 2 passes through the opening 6 formed in these walls 3, 4. The introducer tip may include a piercing shape and/or electromagnetically or thermally enhanced cutting features to assist in forming the opening 6. Once the distal arms 14 of the ring device 9 are in the distal lumen, the distal ring slide control 23 may be proximally moved to actuate the distal arms into a partially actuated ring shape. The distal tissue wall 4 thus held may be drawn back proximally if necessary such that the proximal arms 13 reside within the first lumen. Pushing the proximal ring slide control 24 gradually distally causes partial actuation of the proximal arms 13. If the positioning is correct, the slide controls 23, 24 may be fully slid, causing the proximal and distal arms 13, 14 to be fully actuated. If the ring device 9 is provided with an own latching mechanism, it is automatically latched in its fully actuated configuration, otherwise sliding the latching slide control 45 distally, the snapper part 42 enters within the inner diameter of the ring device 9 and snap engages the distal and proximal rings thereof. It is now possible to disengage the catches 30, 35 that hold the applier 1 to the ring device 9 by rotating the release control 37 which causes the catches to retract radially. Then, the distal tip 5 of the applier is withdrawn from the ring device 9 leaving it deployed to form the anastomotic attachment. Over time, the tissue walls 3, 4 permanently heal together and the ring device 9 may be passed out of the digestive tract, especially if biofragmentable.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, aspects of the invention have application to surgical procedures performed endoscopically and laparoscopically, as well as an open procedure. Use herein of one of these or similar terms should not be construed to limit the present invention for use in only one category of surgical procedure.

For another example, although bariatric procedures for bypassing portions of a gastrointestinal tract are depicted, it should be appreciated that other surgical procedures may benefit by an anastomotic applier and ring device having aspects described herein, such as for the bile duct and vascular bypasses.

What is claimed is:

1. An applier for an anastomosis ring device of the type having proximal, center, and distal rings connected respectively by proximal and distal hinged arms the hinged arms having a generally oblong radially retracted shape when the ring device is un-actuated and a folded radially protruding shape when the ring device is actuated, the applier comprising:

an elongate implement portion and a handle connected to the implement portion;

a distal actuating member comprising catch means which, in a lock position, protrudes radially outward to engage the distal ring;

a proximal actuating member adapted to engage the proximal ring;

an actuation mechanism arranged at the handle and configured to cause the proximal and distal actuating members to move towards each other along a longitudinal axis (X) of the implement portion to approximate the proximal and distal rings causing actuation of the hinged arms, wherein the distal actuating member is rotatable about said longitudinal axis (X) from said lock position to a release position thereby sliding along a deviating surface at the implement portion which is configured to urge said catch means radially inward to disengage it from the distal ring; and wherein the implement portion comprises a substantially cylindrical housing with axially extending distal window slots and the distal actuating member comprises a shaft slidably received inside the housing and a plurality of distal catches protrude outward from the shaft and extend through the distal window slots such that they engage the distal ring of the anastomotic ring device when in said lock position, said distal catches being configured to be deviated radially inward by lateral edges of the distal window slots in response to rotation of the distal actuating member from said lock position to said release position.

2. An applier according to claim 1, wherein the actuation mechanism is adapted to move the proximal actuating member distally and to move the distal actuating member proximally causing actuation of the hinged arms of the ring device while leaving the central ring substantially stationary on the implement portion.

3. An applier according to claim 1, wherein the actuation mechanism is adapted to axially translate the proximal actuating member independently from the axial translation of the distal actuating member and vice versa.

4. An applier according to claim 1, wherein the proximal actuating member comprises a distally facing stationary arresting surface formed at the implement portion and adapted to engage the proximal ring and the actuating mechanism is adapted to proximally translate the distal actuating member towards said arresting surface.

5. An applier according to claim 1, wherein the cylindrical housing further comprises a plurality of axially extending proximal window slots and the proximal actuating member comprises a shaft slidably received inside the housing and a plurality of proximal catches protrude outward from the shaft and extend through the proximal window slots such that they engage the proximal ring of the anastomotic ring device when in said lock position, said proximal catches being configured to be deviated radially inward by lateral edges of the proximal window slots in response to rotation of the proximal actuating member from said lock position to said release position.

6. An applier according to claim 1, wherein said catches are substantially fin shaped and, in the lock position, said fins are inclined in a direction opposite the direction of rotation of the actuating member from the lock position to the release position such as to facilitate the inward deviation of the fins by the lateral edges of the window slots.

7. An applier according to claim 1, wherein the proximal and distal actuating members are arranged axially slidably to one another but coupled in rotation about the longitudinal axis (X) such that the distal and proximal catches can be simultaneously brought in the release position by a single common rotational movement of both actuating members with respect to the housing.

8. An applier according to claim 1, comprising a central actuating member arranged between the proximal and distal actuating member and having catch means adapted to engage the central ring of the ring device to control its position during the actuating movement of the distal and/or proximal actuating members, said central actuating member being rotatable about the longitudinal axis (X) from a lock position to a release position thereby sliding along a deviating surface at the implement portion which is configured to urge the catch means radially inward to disengage it from the central ring.

9. An applier according to claim 8, wherein the central actuating member itself can also be axially moved proximally towards the proximal actuating member and/or distally towards the distal actuating member by means of a central ring slide control.

10. An applier according to claim 8, wherein the central and distal actuating members or the central distal and proximal actuating members are arranged in an axially slidable but rotationally coupled relationship, such that the distal central and proximal catches can be simultaneously brought in their release position by a single common rotational movement of all actuating members with respect to the housing.

11. An applier according to claim 1, comprising a latching mechanism adapted to carry a detachable snapper part separate from the ring device and suitable to snap connect the proximal ring with the distal ring in order to latch the ring device (9) in its actuated configuration.

12. An applier according to claim 11, wherein the latching mechanism comprises one or more longitudinally translatable push portions arranged proximally with respect to the proximal catches or the proximal arresting surface and adapted to engage a proximal end surface of the snapper part and to push the snapper part distally in snap engagement with the anastomotic ring device.

13. An applier according to claim 12, in which the applier is equipped with said snapper part and the snapper part comprises an annular proximal shoulder suitable to engage the proximal end surface of the proximal ring and a longitudinal portion which protrudes distally from the proximal shoulder and forms elastically supported snapper teeth extending radially outwardly from the longitudinal portion to enable snap engagement of the distal ring, wherein said longitudinal portion of the snapper part define slots in alignment with the proximal catches or arresting surfaces and with the distal catches such that the snapper part can be pushed in engagement with the ring device without interfering with the actuating members.

14. An applier according to claim 13, in which the snapper part is adapted to latch the ring device at different adjustable distances between the proximal ring and the distal ring.

15. An applier according to claim 14, in which the snapper part comprises a plurality of snapper teeth arranged in a row which extends in the longitudinal direction of the longitudinal portion such that the distances between the annular proximal shoulder and the different snapper teeth of a same row correspond to different adjustable distances between the proximal and distal rings of the ring device.

16. An applier according to claim 14, in which the annular proximal shoulder of the snapper part comprises a distally projecting externally threaded adjusting portion which mates an internal thread provided at a proximal base of the longitudinal portion such that the distance between the shoulder and the snapper teeth is adjustable by screwing the adjusting portion (50) more or less into the longitudinal portion.

17. An applier according to claim 16, in which also the threaded adjusting portion is slotted in order to not interfere with the proximal catches or arresting surfaces during latching of the ring device.

18. An applier according to claim 12, in which the push portions are adapted to rotate about the longitudinal axis (X) and to engage the annular shoulder of the snapper part so that said rotational adjusting movement causes the annular shoulder to adjustably screw in the longitudinal portion.

* * * * *